(12) United States Patent
Abe

(10) Patent No.: US 8,066,696 B2
(45) Date of Patent: Nov. 29, 2011

(54) OPHTHALMIC LASER TREATMENT APPARATUS

(75) Inventor: Hitoshi Abe, Okazaki (JP)

(73) Assignee: Nidek Co., Ltd., Gamagori-shi (JP)

( * ) Notice: Subject to any disclaimer, the term of this patent is extended or adjusted under 35 U.S.C. 154(b) by 420 days.

(21) Appl. No.: 12/010,826

(22) Filed: Jan. 30, 2008

(65) Prior Publication Data
US 2008/0188838 A1    Aug. 7, 2008

(30) Foreign Application Priority Data
Jan. 30, 2007    (JP) .................................. 2007-020116

(51) Int. Cl.
*A61B 18/20*    (2006.01)
(52) U.S. Cl. .................................. 606/4; 606/6; 606/10
(58) Field of Classification Search .................. 606/4–6, 606/10–12
See application file for complete search history.

(56) References Cited

U.S. PATENT DOCUMENTS

| | | | |
|---|---|---|---|
| 4,724,522 A * | 2/1988 | Belgorod | 606/5 |
| 5,549,596 A | 8/1996 | Latina | |
| 6,066,127 A | 5/2000 | Abe | |
| 6,099,522 A * | 8/2000 | Knopp et al. | 606/10 |
| 6,235,014 B1 * | 5/2001 | Abe et al. | 606/4 |
| 6,319,274 B1 | 11/2001 | Shadduck | |
| 6,346,100 B1 * | 2/2002 | Tano et al. | 606/10 |
| 6,391,021 B1 * | 5/2002 | Mueller et al. | 606/7 |
| 7,033,346 B2 * | 4/2006 | Previn et al. | 606/4 |
| 2007/0213693 A1 * | 9/2007 | Plunkett | 606/6 |
| 2008/0015553 A1 * | 1/2008 | Zacharias | 606/4 |

FOREIGN PATENT DOCUMENTS

| | | |
|---|---|---|
| JP | A-59-14848 | 1/1984 |
| JP | A-2-271581 | 11/1990 |
| JP | A-11-104145 | 4/1999 |
| JP | A-11-332902 | 12/1999 |

* cited by examiner

*Primary Examiner* — Ahmed Farah
(74) *Attorney, Agent, or Firm* — Oliff & Berridge, PLC

(57) ABSTRACT

An ophthalmic laser treatment apparatus, which allows SLT to be performed by a laser source not having a Q-switch which emits a continuous wave laser beam, has a laser source capable of emitting a continuous wave visible laser beam to be absorbed into pigment cells of trabecular meshwork, an irradiation optical system for directing the laser beam to a patient's eye so as to irradiate the eye with the laser beam, a device for pulsing the laser beam by controlling a driving duration of the laser source or opening and closing durations of a shutter in the irradiation optical system, a device capable of setting an irradiation duration of the laser beam within a range of 0.1 msec to 5 msec in order to perform Selective Laser Trabeculoplasty, and a device capable of setting irradiation energy density of the laser beam within a range of 1 $J/cm^2$ to 8.5 $J/cm^2$.

6 Claims, 4 Drawing Sheets

OPHTHALMIC LASER TREATMENT APPARATUS

BACKGROUND OF THE INVENTION

1. Field of the Invention

The present invention relates to an ophthalmic laser treatment apparatus for performing Selective Laser Trabeculoplasty by irradiating a patient's eye with a laser beam.

2. Description of Related Art

Conventionally, there is known an apparatus for performing Selective Laser Trabeculoplasty (SLT) in which an Nd:YAG laser source having a Q-switch and a wavelength conversion element is included, and reduction in intraocular pressure is induced by irradiating trabecular meshwork of a patient's eye with a visible laser beam having an extremely short pulse width of the order of nanoseconds which is generated by the Q-switch and emitted (see U.S. Pat. No. 5,549,596). Different from Argon Laser Trabeculoplasty which induces reduction in intraocular pressure by coagulating (photocoagulating) trabecular meshwork with a laser beam and constricting a part of the trabecular meshwork, SLT allows treatment by re-irradiation because SLT does not have an effect on a net-like structure of the trabecular meshwork.

However, the conventional apparatus for SLT uses the laser source having the Q-switch in order to emit the laser beam having the extremely short pulse width of the order of nanoseconds, but does not use a laser source capable of emitting a continuous wave laser beam. In addition, such an apparatus is dedicated only to SLT and cannot be used for other treatment.

SUMMARY OF THE INVENTION

An object of the invention is to overcome the problems described above and to provide an ophthalmic laser treatment apparatus which allows SLT to be performed with the use of a laser source not having a Q-switch which emits a continuous wave laser beam.

To achieve the objects and in accordance with the purpose of the present invention, an ophthalmic laser treatment apparatus has a laser source capable of emitting a continuous wave visible laser beam to be absorbed into pigment cells of trabecular meshwork, an irradiation optical system for directing the laser beam to a patient's eye so as to irradiate the patient's eye with the laser beam, pulsing means for pulsing the laser beam with which the patient's eye is to be irradiated by controlling a driving duration of the laser source or controlling opening and closing durations of a shutter disposed in the irradiation optical system, irradiation duration setting means capable of setting an irradiation duration of the laser beam within a range of 0.1 msec to 5 msec in order to perform Selective Laser Trabeculoplasty, and irradiation energy setting means capable of setting irradiation energy density of the laser beam within a range of 1 J/cm$^2$ to 8.5 J/cm$^2$.

In another aspect of the present invention, an ophthalmic laser treatment apparatus has a laser source capable of emitting a continuous wave visible laser beam to be absorbed into pigment cells of trabecular meshwork, an irradiation optical system for directing the laser beam to a patient's eye so as to irradiate the patient's eye with the laser beam, and a control part which controls a driving duration of the laser source so as to pulse the laser beam with which the patient's eye is to be irradiated, wherein the control part is capable of setting an irradiation duration of the laser beam within a range of 0.1 msec to 5 msec in order to perform Selective Laser Trabeculoplasty, and is capable of setting irradiation energy density of the laser beam within a range of 1 J/cm$^2$ to 8.5 J/cm$^2$.

Yet, in another aspect of the present invention, an ophthalmic laser treatment apparatus has a laser source capable of emitting a continuous wave visible laser beam to be absorbed into pigment cells of trabecular meshwork, an irradiation optical system for directing the laser beam to a patient's eye so as to irradiate the patient's eye with the laser beam, a shutter disposed in the irradiation optical system, a shutter driving device which opens and closes the shutter, and a control part which controls the shutter driving device so as to control opening and closing durations of the shutter in order to pulse the laser beam with which the patient's eye is to be irradiated, wherein the control part is capable of setting an irradiation duration of the laser beam within a range of 0.1 msec to 5 msec in order to perform Selective Laser Trabeculoplasty, and is capable of setting irradiation energy density of the laser beam within a range of 1 J/cm$^2$ to 8.5 J/cm$^2$.

Additional objects and advantages of the invention are set forth in the description which follows, are obvious from the description, or may be learned by practicing the invention. The objects and advantages of the invention may be realized and attained by the apparatus in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
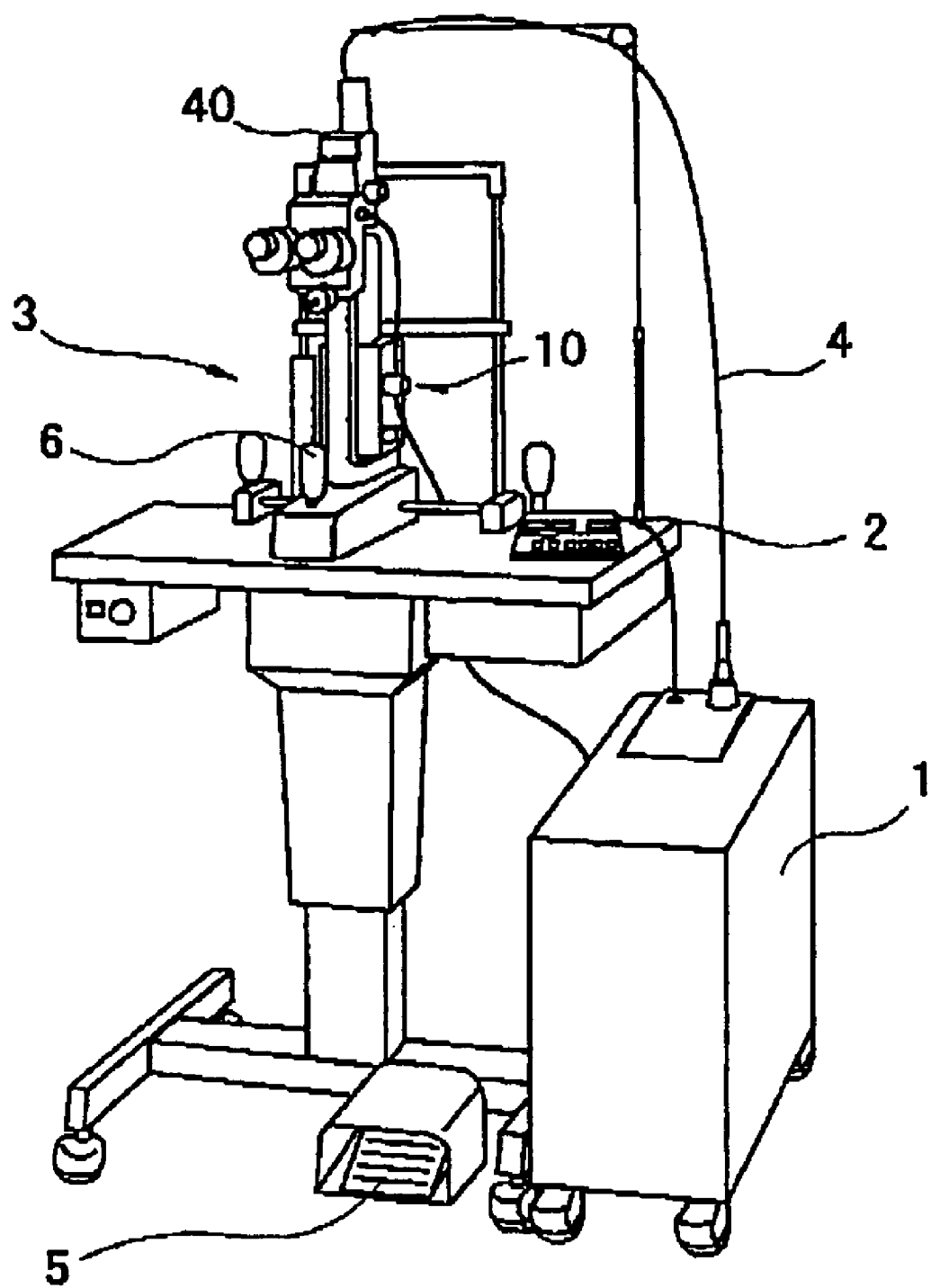
FIG. 1 is a schematic external view showing a laser treatment apparatus according to a preferred embodiment of the present invention.
Figure 2:
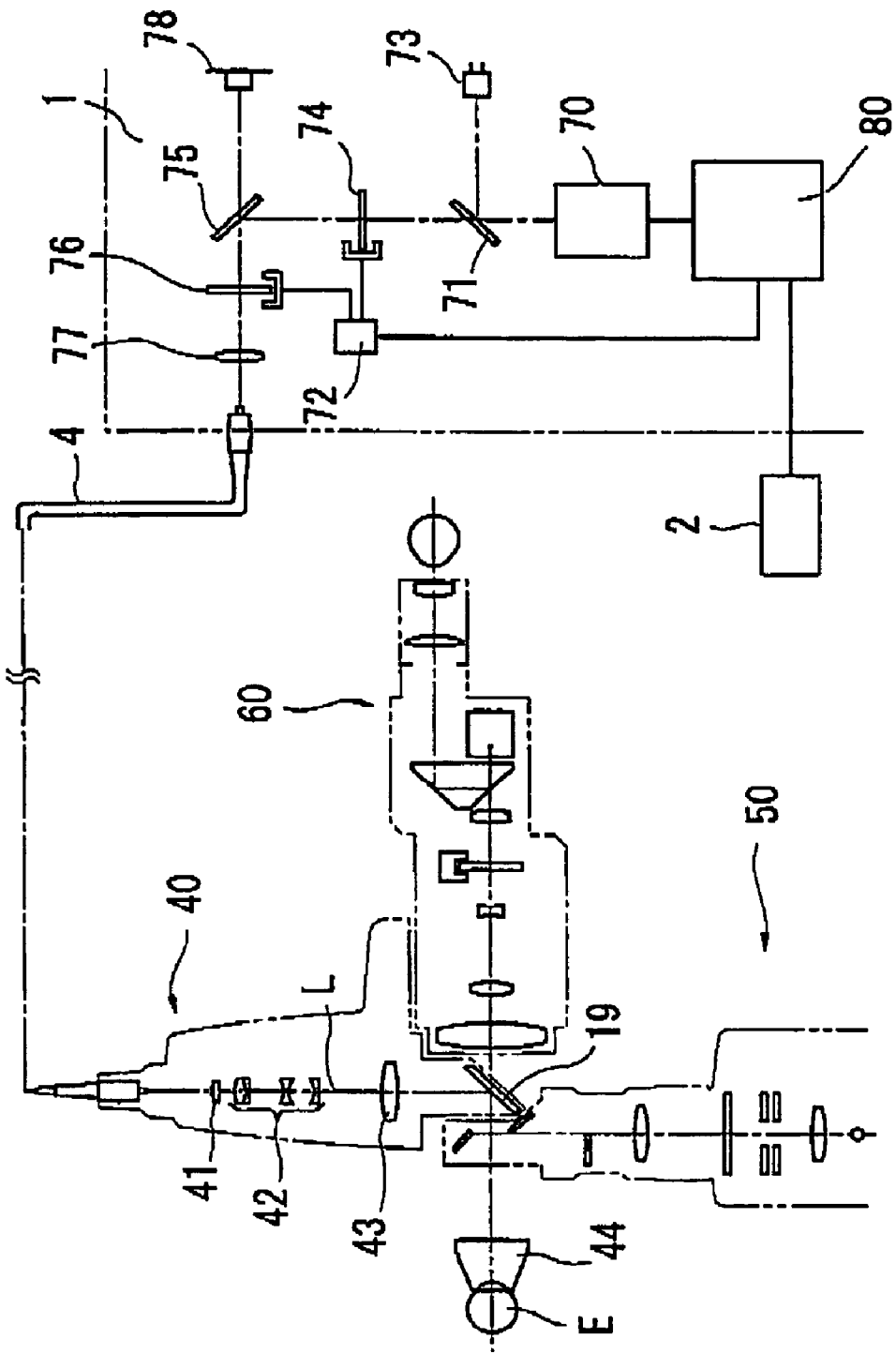
FIG. 2 is a schematic view showing an optical system and a control system of the laser treatment apparatus.

A detailed description of one preferred embodiment of an ophthalmic laser treatment apparatus embodied by the present invention is provided below with reference to the accompanying drawings. FIG. 1 is a schematic external view showing the laser treatment apparatus according to the preferred embodiment of the present invention. FIG. 2 is a schematic view showing an optical system and a control system of the laser treatment apparatus.

A main body 1 of the laser treatment apparatus incorporates a laser source 70 which emits a continuous wave visible treatment laser beam (hereinafter, referred to as the treatment beam), a laser source 78 which emits an aiming laser beam (hereinafter, referred to as the aiming beam), and other mechanisms. The laser source 70 has a semiconductor laser as an excitation light source, an Nd:YAG crystal as a laser medium, a resonator optical system such as a total reflection mirror and an output mirror, a wavelength conversion element which converts a laser beam having a wavelength of 1064 nm (infrared) into a frequency-doubled (second harmonic) laser beam having a wavelength of 532 nm (green), and other mechanisms. In SLT and photocoagulation, energy of a laser beam is preferably absorbed into pigment-containing cells, and therefore, a visible laser beam is used as the treatment beam. Though the green laser beam is used as the treatment beam in the preferred embodiment of the present invention, a yellow, orange or red laser beam may be used, and a laser source capable of emitting a laser beam with a color (wavelength) to be used can be used.

A setting part 2 is used for setting irradiation conditions and other factors of the treatment beam. A slit lamp 3 incorporates an irradiation optical system (beam directing optical system) of the treatment beam and the aiming beam, an illumination optical system, an observation optical system, and other mechanisms. A foot switch 5 is used for emitting a trigger signal for irradiation of the treatment beam. A joystick 6 is used for moving the slit lamp 3 on a table. A spot size adjusting knob 10 is used for setting a spot size (diameter) of the treatment beam within a range of 50 μm to 1000 μm.

Concerning the treatment beam emitted from the laser source 70, a part thereof is reflected by a beam splitter (half mirror) 71 which transmits a large part of the treatment beam and reflects a part thereof, and enters an energy sensor 73 which detects output energy (power) of the treatment beam.

When the trigger signal is emitted by the foot switch 5 (i.e., when the trigger signal is inputted to a control part 80), a first safety shutter 74 is removed from an optical path by a shutter driving device 72 so as to allow passage of the treatment beam. When abnormal conditions are encountered, a second safety shutter 76 is inserted into the optical path by the shutter driving device 72 so as to block the passage of the treatment beam (and the aiming beam). Opening and closing states of the shutters 74 and 76 are detected by a shutter sensor not shown.

An irradiation duration of the treatment beam can be varied by controlling a lighting duration of the semiconductor laser of the laser source 70 by means of the control part 80. In addition, the irradiation duration of the treatment beam can be varied also by controlling opening and closing durations of the shutter 74 by the shutter driving device 72 by means of the control part 80, instead of controlling the lighting duration of the semiconductor laser. By controlling the laser source 70 or the shutter 74 by means of the control part 80 as described above, the laser beam is pulsed.

For the laser source 70, a fiber laser having a semiconductor laser as an excitation light source may be used.

The aiming beam emitted from the laser source 78 is made coaxial with the treatment beam by a beam combiner (dichroic mirror) 75 which reflects the treatment beam and transmits the aiming beam.

A condenser lens 77 makes the beams converge and enter an entrance end face of an optical fiber 4. The beams directed by the optical fiber 4 are directed to an irradiation optical system unit 40 of the slit lamp 3.

The beams directed to the irradiation optical system 40 pass through a relay lens 41, a zoom lens (variable power optical system) 42 which is movable in the direction of an optical axis L so as to vary the spot size of the treatment beam (and the aiming beam), and an objective lens 43, are reflected by a total reflection mirror 19, and pass through a contact lens 44 so as to irradiate a diseased part of a patient's eye E. The irradiation optical system unit 40 is provided with a mechanism to move the zoom lens 42 along the optical axis L in response to the rotation of the knob 10, which mechanism is not shown. This configuration makes the spot size of the treatment beam (and the aiming beam) variable within the range of 50 μm to 1000 μm. The knob 10 is attached to an encoder not shown which is connected to the control part 80, and a rotation amount of the knob 10 is obtained by the encoder and transmitted to the control part 80. The control part 80 obtains the set spot size based on a signal from the encoder.

An illumination optical system 50 includes a light source for illumination, a condenser lens, a slit plate, a projection lens, and other mechanisms. An observation optical system 60 includes an objective lens, a variable power optical system, a protection filter, erecting prisms, a field diaphragm, an eyepiece, and other mechanisms.

The control part 80 is connected with the laser sources 70 and 78, the energy sensor 73, the shutter driving device 72, the shutter sensor, the setting part 2, the foot switch 5, and other mechanisms.

Figure 3:
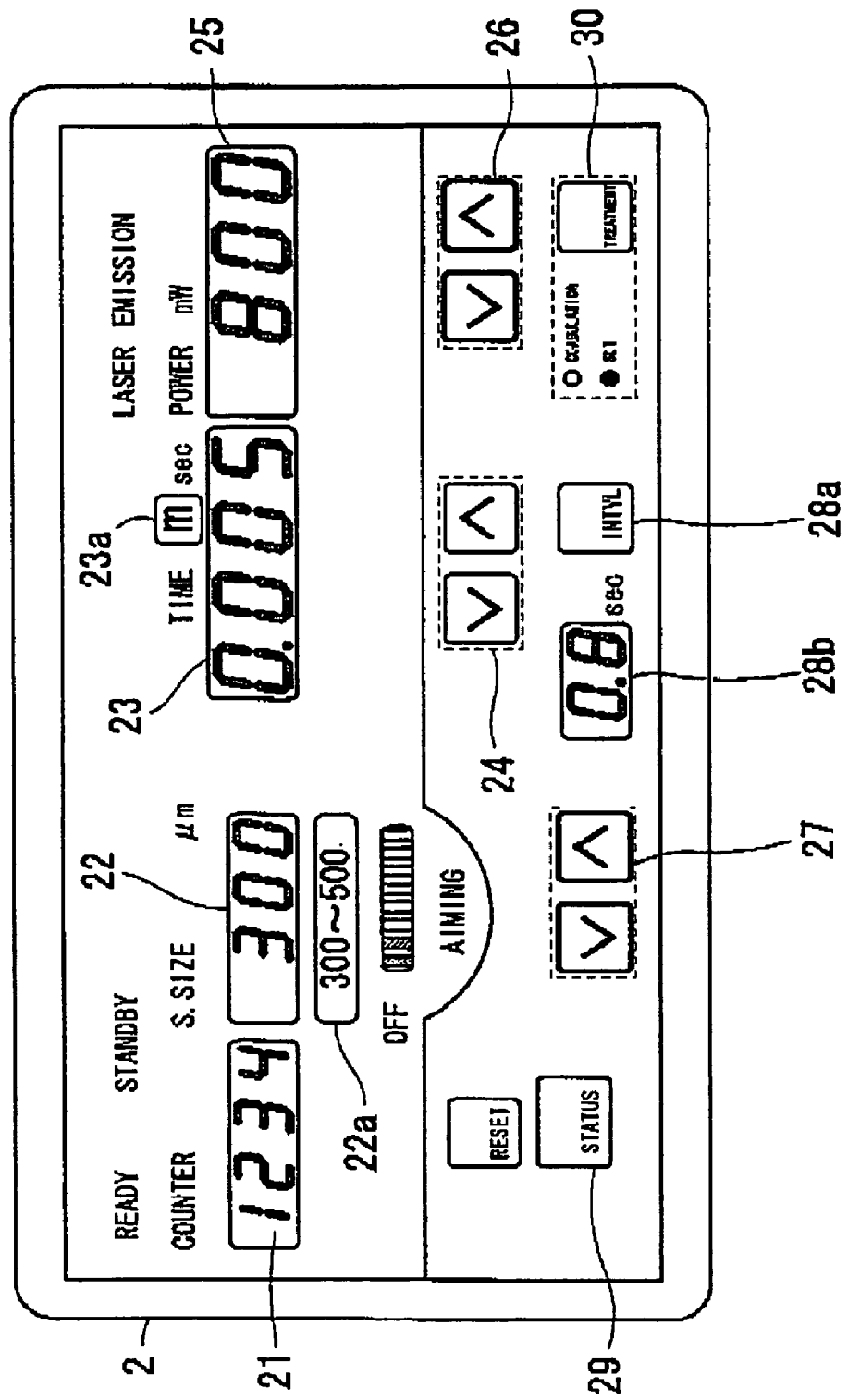
FIG. 3 is a schematic external view showing a setting part of the laser treatment apparatus.

FIG. 3 is a schematic external view showing the setting part 2. A display part 21 displays the number of times the irradiation of the treatment beam is made, and a display part 22 displays the spot size of the treatment beam. The spot size can be set within the range of 50 μm to 1000 μm in increments of 10 μm by means of the knob 10, and the signal of the spot size set by the knob 10 is inputted to the control part 80. A display part 22a displays a recommended range of the spot size. A display part 23 displays the irradiation duration of the treatment beam, and a switch 24 is used for setting the irradiation duration. A display part 23a indicates that conversion of the time unit of the irradiation duration displayed on the display part 23 is made. On the display part 23a a letter "m" indicating a prefix "milli-" is arranged to be displayed by lighting. When the letter "m" is lit, the time unit of the irradiation duration displayed on the display part 23 is millisecond, and when the letter "m" is not lit, the time unit of the irradiation duration displayed on the display part 23a is second. The control part 80 makes switching of the display upon receipt of a signal from the switch 24. The irradiation duration which can be displayed on the display part 23 and the display part 23a (which can be set by the switch 24) is within a range of 0.1 msec to 3 sec. A display part 25 displays irradiation energy (power) of the treatment beam, and a switch 26 is used for setting the irradiation energy. An aiming switch 27 is used for adjusting brightness of the aiming beam. A switch 28a is used for setting an irradiation interval of the treatment beam successively emitted during the time when the foot switch 5 is depressed, and a display part 28b displays the set irradiation interval. The irradiation interval can be set within a range of 0.1 sec to 1 sec in increments of 0.1 sec. A switch 29 is used for performing switching between a status in which the irradiation of the treatment beam is permitted and a status in which the irradiation of the treatment beam is not permitted.

Next, a description of SLT will be provided. In the apparatus according to the preferred embodiment of the present invention, a settable range of the irradiation duration in photocoagulation to be described later is from 10 msec to 3 sec, while a settable range of the irradiation duration in SLT is from 0.1 msec to 5 msec which does not allow photocoagulation. The irradiation energy is adjusted in accordance with the set irradiation duration. For example, the irradiation energy is adjusted within a range of 0.5 W to 2 W. In addition, the spot size is set based on the type of treatment and other factors. In SLT, the spot size is set within a range of 300 μm to 500 μm.

A description of experiments of SLT will be provided hereinafter. The irradiation conditions of the treatment beam were set such that the irradiation duration was 1 msec or 5 msec, the irradiation energy was 0.8 W to 1.2 W, and the spot size was 300 μm. Trabecular meshwork of an extracted eye was irradiated with the treatment beam under the irradiation conditions, and an irradiated state of the trabecular meshwork was observed through a microscope. In either of the case of the irradiation duration of 1 msec and the case of the irradiation duration of 5 msec, damages or other problems made by heat effect were not observed in tissue of the trabecular meshwork. Accordingly, it is considered that pigment cells of the trabecular meshwork have been selectively removed.

Next, an eye with ocular hypertension or an eye with glaucoma was irradiated with the treatment beam under the same conditions as described above, and the variation in intraocular pressure was measured over time. Results of the measurement show reduction in the intraocular pressure as compared to the intraocular pressure before the irradiation of the treatment beam. A scar made by heat effect of Argon Laser Trabeculoplasty was not made in a portion irradiated with the treatment beam.

Based on the experiment results as mentioned above, it is discovered that an SLT effect or a similar effect is achieved by pulsing a continuous wave visible laser beam emitted from a laser source not having a Q-switch, which is conventionally used in photocoagulation, with the irradiation duration of 5 msec or less.

U.S. Pat. No. 5,549,596 uses a laser source having a Q-switch and achieves an SLT effect or a similar effect by the use of a laser beam having an extremely short pulse width of 5 nsec or less. The extremely short pulse beam by the Q-switch increases in irradiation energy explosively (up to the order of a megawatt) during an extremely short period of time, and therefore, energy density thereof is reduced by increasing its spot size, so that an SLT effect or a similar effect is achieved without causing thermal action and mechanical destruction. With a pulse width by the Q-switch in a 10 nsec range which is rather longer than the pulse width of 5 nsec, the explosive increase in the irradiation energy cannot be suppressed, the mechanical destruction is caused strongly, and damage to eye tissue cannot be suppressed. Therefore, that apparatus is used with the pulse width of 5 nsec or less.

In contrast, in SLT by the use of the apparatus according to the present invention, by pulsing the continuous wave laser beam emitted from the laser source not having the Q-switch, which is used in photocoagulation, within the range of 0.1 msec to 5 msec being shorter than the irradiation duration in photocoagulation and far longer than the order of nanoseconds, an SLT effect or a similar effect can be achieved without involving photocoagulation having heat effect.

Energy (power) density by which an SLT effect or a similar effect is achieved is calculated from the experiment results in the following manner. Letting the total energy (power) be indicated by E(J), the set irradiation energy be indicated by P(W) and the set irradiation duration be indicated by d(sec), an equation, E=P·d, is established. Letting an irradiation area based on the set spot size be indicated by S, the energy density D (J/cm$^2$) is calculated as follows.

$$D=E/S=P\cdot d/S$$

In the experiments, the spot size was set to be 300 μm in diameter, and the following expression is established.

$$S=706.5\times 10^{-6} \text{ (cm}^2\text{)}$$

In the experiments where the irradiation durations were set to be d=1 msec and d=5 msec, and the irradiation energy was set to be P=0.8 W to 1.2 W, ranges of the energy density D by which an SLT effect or a similar effect is achieved are calculated to show:

$$D=5.66\sim 8.49 \text{ (J/cm}^2\text{)}$$

where d=5 msec; and $$D=1.13\sim 1.70 \text{ (J/cm}^2\text{)}$$

where d=1 msec.

Based on these calculations, the irradiation energy P, the irradiation duration d and the spot size (irradiation area S) are set so that the energy density D is within a range of about 1.0 J/cm$^2$ to 8.5 J/cm$^2$ at the time of pulsing the continuous wave laser beam, whereby an SLT effect or a similar effect can be achieved.

With regard to the irradiation duration d, pulsing can be performed up to 0.1 msec by controlling a driving duration of the laser-source 70 or controlling the opening and closing durations of the shutter 74 without using the Q-switch. In the case of setting the irradiation duration d to be 0.1 msec, if the spot size is set to be 100 μm in diameter, setting the irradiation energy P to be 0.8 W or more allows the energy density D to be about 1.0 J/cm$^2$ or more. The energy density D in the case of setting the upper limit of the irradiation energy P of the laser source 70 to be 2.0 W becomes about 2.5 J/cm$^2$. In the case of setting the irradiation duration d to be 0.5 msec, even if the spot size is set to be 200 μm in diameter, setting the irradiation energy P to be 0.6 W or more ensures the energy density D to be 1.0 J/cm$^2$ or more.

The spot size of the treatment beam in SLT is preferably larger than that in photocoagulation, and is preferably set within a range of 100 μm to 1 mm. In the case of setting the spot size to be 1 mm, setting the irradiation duration d to be 5 msec and the irradiation energy P to be 1.6 W or more allows the energy density D to be 1.0 J/cm$^2$ or more. The spot size in SLT is preferably within the range of 300 μm to 500 μm. In the case of setting the spot size to be 500 μm, setting the irradiation energy P to be 2.0 W and the irradiation duration d to be 1 msec or more allows the energy density D to be 1.0 J/cm$^2$ or more.

The irradiation duration d in which the continuous wave laser beam is pulsed is preferably set within the range of 0.1 msec to 5 msec, and is more preferably set within a range of 0.5 msec to 1 msec. It is essential only that the relation between the spot size and the irradiation energy P is set so that the energy density D is within the range of about 1.0 J/cm$^2$ to 8.5 J/cm$^2$. As mentioned above, the spot size is preferably set within the range of 300 μm to 500 μm, and it is enough if such setting limits the settable range of the irradiation energy P.

Figure 4:
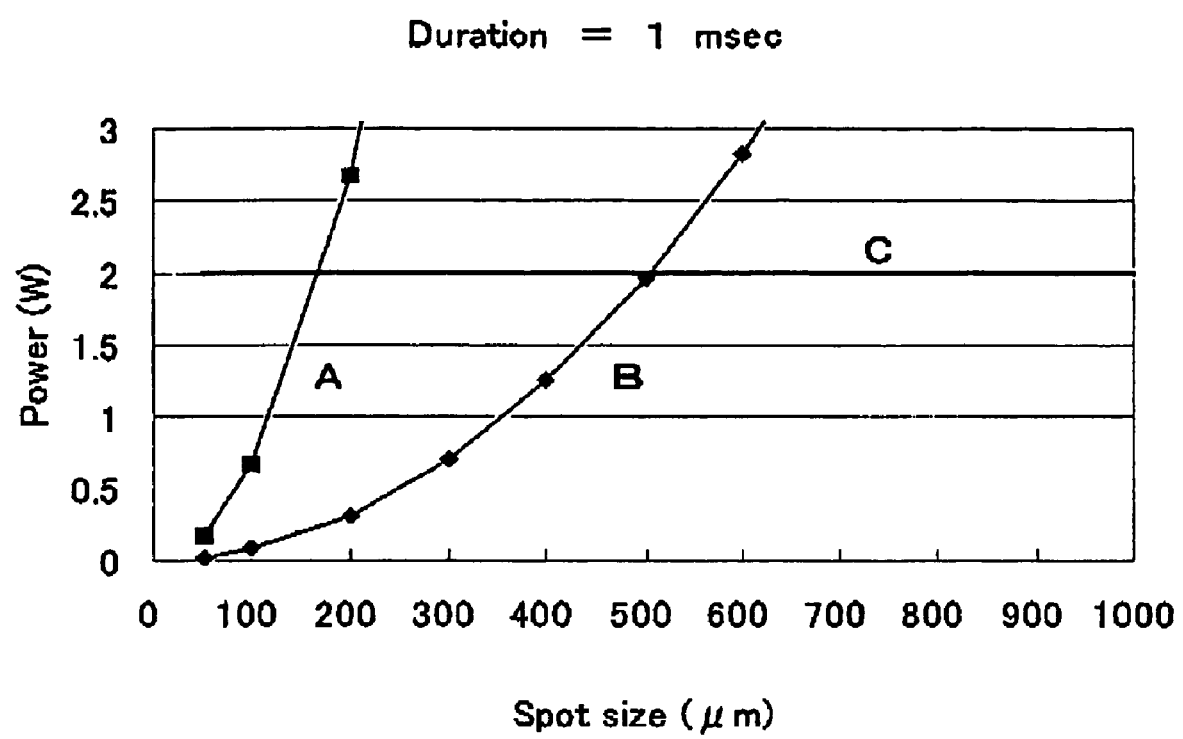
FIG. 4 is a view showing a relation between irradiation energy and a spot size in the case of setting an irradiation duration to be 1 msec.

The relation between the irradiation energy and the spot size may be set based on the relational diagram shown in FIG. 4. FIG. 4 is a view showing the relation between the irradiation energy and the spot size when the irradiation duration is set to be 1 msec. The curved line A in FIG. 4 is a plot in the case of setting the energy density D to be 8.5 J/cm$^2$, and the curved line B in FIG. 4 is a plot in the case of setting the energy density D to be 1.0 J/cm$^2$. These plots are calculated based on the above-mentioned relational expression of the energy density D, the irradiation energy P, the irradiation duration d, and the spot size (the irradiation area S) The straight line C is a plot of the irradiation energy P at 2 W, which indicates the upper limit of the irradiation energy P in the apparatus according to the preferred embodiment of the present invention.

The range which is defined by (interposed between) the curved line A and the curved line B and of which the upper limit is defined by the straight line C illustrates a range for setting the irradiation energy P and the spot size that determine the energy density D. Based on such data, the irradiation conditions of the treatment beam in SLT according to the preferred embodiment of the present invention are determined. For example, it is shown that the irradiation energy P may be set within a range of 0.7 W to 2 W in the case of setting the spot size to be 300 μm. Likewise, it is shown that the irradiation energy P may be set within a range of 1.2 W to 2 W in the case of setting the spot size to be 400 μm.

As mentioned above, the irradiation duration d is set, the range of the energy density D is defined, the relation between the irradiation energy P and the spot size is plotted or expressed mathematically, and the irradiation energy P and the spot size are determined so as to meet the range of the energy density D.

Next, a description of an operation of SLT will be provided. With the use of the switch 24, the irradiation duration is set within the range of 0.1 msec to 5 msec. In the case of setting the irradiation duration to be 1 msec, a recommended value of the spot size in accordance with the irradiation duration is displayed on the display part 22a. When the irradiation duration and the spot size are set, a recommended value of the irradiation energy is calculated by the control part 80 and displayed on the display part 25. In the calculation, the control part 80 limits the range of the irradiation energy settable by the switch 26 so as to satisfy the energy density of 1 $J/cm^2$ to 8.5 $J/cm^2$. When the irradiation energy is set beyond the settable range, the value displayed on the display part 25 blinks or changes in color (i.e., an alert is indicated).

Next, the status in which the irradiation of the treatment beam is permitted is set by the switch 29, alignment of the patient's eye is performed, and the contact lens 44 is fixed to the patient's eye. Then, the diseased part of the patient's eye illuminated by the illumination optical system 50 is observed through the observation optical system 60, the aiming beam is aimed at the diseased part, and the diseased part is irradiated with the treatment beam.

As mentioned above, SLT can be performed by the use of the laser source not having the Q-switch. In addition, the treatment by the use of the continuous wave laser beam can be performed as the laser source does not have the Q-switch.

Next, a brief description of photocoagulation by the laser source 70 will be provided. There is known a photocoagulation apparatus which has a laser source emitting a continuous wave visible laser beam, and performs photocoagulation by irradiating a diseased part such as a fundus with the laser beam (see Japanese Patent Application Unexamined Publication No. Sho 59-14848).

A surgeon sets irradiation conditions of the laser beam with the use of the switches of the setting part 2. In photocoagulation, coagulation burns are intended to be produced, and therefore, a range of an irradiation duration is set to be longer than that of SLT. The irradiation duration can be set within a range of 10 msec to 3 sec. Irradiation energy (power) can be set within a range of 0.05 W to 2 W. In addition, a spot size suitable for the treatment is set by the knob 10. In retinal photocoagulation, the spot size within a range of 100 μm to 300 μm is widely used on average.

With the irradiation conditions being set, the contact lens 44 is fixed to the patient's eye. Then, the diseased part of the patient's eye illuminated by the illumination optical system 50 is observed through the observation optical system 60, the aiming beam is aimed at the diseased part, and the diseased part is irradiated with the treatment beam.

Because the irradiation duration of photocoagulation is different from that of SLT, a switch 30 for performing selection between a photocoagulation mode and an SLT mode is preferably provided to the setting part 2. When the photocoagulation mode is selected, the control part 80 limits the irradiation duration of the treatment beam to be settable within the range of 10 msec to 3 sec. When the SLT mode is selected, the control part 80 limits the irradiation duration of the treatment beam to be settable within the range of 0.1 msec to 5 msec. When the irradiation duration is set, the recommended value of the spot size in accordance with the set irradiation duration is displayed on the display part 22a. In addition, when the irradiation duration and the spot size are set, the recommended value of the irradiation energy is calculated by the control part 80 and displayed on the display part 25. In this calculation, the range of the irradiation energy settable by the switch 26 is limited by the control part 80 so as to satisfy the energy density of 1 $J/cm^2$ to 8.5 $J/cm^2$.

As mentioned above, SLT can be performed with the use of the laser source not having the Q-switch. In addition, using the laser source which emits the continuous wave visible laser beam for photocoagulation and adjusting the irradiation duration allow one apparatus to perform both photocoagulation and SLT.

In the preferred embodiment of the present invention, the switching between photocoagulation and SLT is performed by the switch, however, it is not limited thereto. Selection between photocoagulation and SLT can be performed by the setting of the irradiation duration.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic laser treatment apparatus comprising:
    a laser source arranged to emit a visible laser beam having a wavelength range that is absorbed into a retina and into pigment cells of trabecular meshwork as a continuous wave;
    an irradiation optical system for directing the laser beam to a patient's eye so as to irradiate the patient's eye with the laser beam;
    pulsing means for making the continuous wave laser beam into a pulsed laser beam having a pulse width within a range of 0.1 msec to 5 msec by controlling a driving duration of the laser source or controlling opening and closing durations of a shutter disposed in the irradiation optical system;
    a selecting switch arranged to perform selection between a continuous wave mode of irradiating the continuous wave laser beam for an operative method including retinal photocoagulation and a pulse mode of irradiating the pulsed laser beam for an operative method including Selective Laser Trabeculoplasty (SLT); and
    irradiation duration setting means that sets an irradiation duration of 10 msec or more when the continuous wave mode is selected, and sets the pulse width within the range of 0.1 msec to 5 msec when the pulse mode is selected.

2. The ophthalmic laser treatment apparatus according to claim 1, further comprising:
    spot size setting means that sets a spot size of the laser beam to be within a predetermined range; and
    irradiation energy setting means that sets energy density within the range of 1 $J/cm^2$ to 8.5 $J/cm^2$ based on the set spot size.

3. The ophthalmic laser treatment apparatus according to claim 1, wherein the irradiation duration setting means comprises a display arranged to display a range of the irradiation duration settable for the selected mode.

4. The ophthalmic laser treatment apparatus according to claim 1, wherein the selecting switch comprises a switch arranged to select a treatment mode, and the pulse mode comprises a Selective Laser Trabeculoplasty (SLT) mode.

5. The ophthalmic laser treatment apparatus according to claim 1, wherein the selecting switch comprises a switch arranged to select a treatment mode and the continuous wave mode comprises a retinal photocoagulation mode.

6. The ophthalmic laser treatment apparatus according to claim 1, wherein the selecting switch comprises a switch arranged to set the irradiation duration.

* * * * *